(12) United States Patent
Lin et al.

(10) Patent No.: US 7,030,970 B2
(45) Date of Patent: Apr. 18, 2006

(54) OPTICAL APPARATUS FOR MEASURING THE VELOCITY OF FLOWING BIOMATERIALS

(75) Inventors: Kang-Ping Lin, Jungli (TW); Yuh-Ping Tong, Hsinchu (TW); Alex Hsieh, Hsinchu (TW); Mang-Yi Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 212 days.

(21) Appl. No.: 10/743,878

(22) Filed: Dec. 24, 2003

(65) Prior Publication Data

US 2004/0145750 A1 Jul. 29, 2004

(30) Foreign Application Priority Data

Dec. 27, 2002 (TW) ................................ 91137769 A

(51) Int. Cl.
*G01P 3/36* (2006.01)
*G01N 21/85* (2006.01)
(52) U.S. Cl. ........................................ 356/28; 250/573
(58) Field of Classification Search ................. 356/28, 356/28.5, 497; 250/573, 356.1, 356.2; 73/861
See application file for complete search history.

(56) References Cited

U.S. PATENT DOCUMENTS

| 5,982,478 A | * | 11/1999 | Ainsworth et al. ............ 356/28 |
| 6,642,999 B1 | * | 11/2003 | Arndt et al. ................... 356/28 |
| 6,653,651 B1 | * | 11/2003 | Meinhart et al. ............ 250/573 |
| 2002/0093641 A1 | * | 7/2002 | Ortyn et al. .................. 356/28 |

* cited by examiner

*Primary Examiner*—Thomas H. Tarcza
*Assistant Examiner*—Isam Alsomiri
(74) *Attorney, Agent, or Firm*—Bacon & Thomas, PLLC

(57) ABSTRACT

An optical apparatus for measuring the velocity of flowing biomaterials is disclosed, which has a coherent light source for projecting a light beam with low coherent length; a reference member having mirrors for periodically reflecting lights thereon; a photo detector for receiving photo signals; a splitter for splitting said light beam from said coherent light source into a reference beam and a detecting beam. The disclosed optical apparatus can save the time for complicate computation and the cost of software or hardware for measuring the flowing velocity of biomaterials, especially the flowing velocity of flowing bloods in vessels.

15 Claims, 3 Drawing Sheets

OPTICAL APPARATUS FOR MEASURING THE VELOCITY OF FLOWING BIOMATERIALS

BACKGROUND OF THE INVENTION

1. Field of the Invention

The present invention relates to an optical apparatus for measuring flow velocity of materials and, more particularly, to an optical apparatus with coherent light source and optical coherence tomography for measuring the relative velocity or absolute velocity of biomaterial flows.

2. Description of Related Art

Currently, conventional measurement of relative flow velocity of blood in blood vessels is frequently achieved by the assistance of blood flow meters. Through measuring the intensity signals of supersonic wave, light or electromagnetic wave reflected from the blood vessels, information of relative blood flow velocity can be obtained after computation through electronic circuit or microprocessors is done. Among them, blood flow meters of optical detection is very helpful for monitoring the micro cycle for blood in a human body after a plastic operation, for diagnosis for the scalded patients or burn patients, for effect evaluation of micro drug cycle, or for body condition analysis of diabetics or sportsmen. However, complicate software or hardware is required for the computation for transferring the detected light intensities into flow velocity information for conventional blood flow meters. Therefore, the cost for measuring the blood flow velocity is high and the time taken for measurement is long.

On the other hand, since there is no common standard for calibrating the flow velocity measured or evaluated from the conventional optical blood flow meters, the flow velocities measured through various conventional blood meters cannot be widely communicated as reliable information now. The exchange of medical information therefore becomes inconvenient for further investigation or diagnosis.

Therefore, it is desirable to provide an improved speech recognition method to mitigate and/or obviate the aforementioned problems.

SUMMARY OF THE INVENTION

The object of the present invention is to provide a non-intruded optical apparatus for measuring the velocity of flowing biomaterials to decrease the computation for transferring light intensity into relative or absolute flow velocity, and to reduce the time for computation and the cost of software or hardware.

The other object of the present invention is to provide a non-intruded optical apparatus for measuring the absolute velocity of flowing biomaterials of different depth in blood vessels or under the skin, to shorten the time for measuring the flow velocity, to facilitate the communication of the medical information of flowing velocities based on the same bases, and to increase the accuracy of velocity measurement.

To achieve the object, the optical apparatus for measuring the velocity of flowing biomaterials of the present invention includes: a coherent light source for projecting a light beam with low coherent length; a reference member having mirrors for periodically reflecting lights thereon; a photo detector for receiving photo signals; a splitter for splitting said light beam from said coherent light source into a reference beam and a detecting beam; wherein said splitter is located between said photo detector and said reference member, said reference beam from said splitter projects on said reference member and reflects back to said photo detector by the refection of said splitter; said detecting beam from said splitter projects on said biomaterials and reflects back to said photo detector by the refection of said splitter; and at least one location of said reference member relative to said splitter is applied as the velocity of said biomaterials flow is measured.

The reference member can be any conventional device or unit that can periodically reflecting lights back to the splitter for reference use. Preferably, the reference members are gears, disks, or wheels deposited with mirrors or reflecting layers for light reflection. More preferably, the reference members are gears with teeth deposited with reflecting layers or mounted with mirrors. The number of the position or the location of the reference member for flow velocity measurement can be either one or more than one. It depends on the purposes of the flow velocity measurement. For example, if only the average relative flow velocity of a specific depth is needed, only one position for measurement is required. However, if information for the flow velocities of various depths in vessels is required, plural positions are applied for measurement. The plural positions or locations of the reference member can be obtained by moving the reference member of the apparatus of the present invention. The path for movement of the reference member is not limited. Preferably, the reference member moved linearly. More preferably, the reference member moves according to the line parallel to the light path between the reference member and the splitter. The reference member can be moved by any mechanism. Preferably, the reference member is moved through a platform. The reference member of the optical apparatus of the present invention can selectively include motors for driving the gears, the discs, or the wheels of the reference member to rotate for periodically reflect the light to the splitter. The rotation velocity of the motor can be controlled through any conventional way. Preferably, the rotation velocity or the rotation speed of the motor depends on a voltage input to the motor. Additionally, the optical apparatus of the present invention can optionally arrange a polarizer in a position between the coherent light source and the splitter to unifying the polarity of the light from the coherent light source and the light of the detecting beam. The polarized light will increase the accuracy of the measurement of the flow velocity of biomaterials. The photo detector of the optical apparatus of the present invention can be any conventional photo detector. Preferably, the photo detector is charge-coupled-device (CCD). The biomaterials suitable for measurement by the optical apparatus of the present invention can be any flowing biomaterials that can reflect the light beam with low coherent length. Preferably, the biomaterials suitable for measurement by the optical apparatus of the present invention are bloods in vessels of animals or human. The coherent length of the light beam from the coherent light source can be any length less than 500 μm. Preferably, the coherent length of the light beam from the coherent light source is less than 100 μm. The coherent light source of the optical apparatus of the present invention can be any light source with short coherent length. Preferably, the coherent light source is an ultrafast laser, a super luminescent diode (SLD), an edge emitting diode laser, an Er-doped super luminescence optical fiber, and a Tm-doped super luminescence optical fiber. The wavelength of the coherent light source is not limited. Preferably, the wavelength of the coherent light source is located in the wavelength region of visible light or of near-infrared radiation. The optical apparatus of the present invention can optionally include an auxiliary mask having a slit and located between said splitter and said photo detector to facilitate the formation of patterns on the photo detector. Preferably, the lights reflected on said photo detector form a pattern of stripes, and the width of said slit is less than a distance between any two adjacent stripes.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
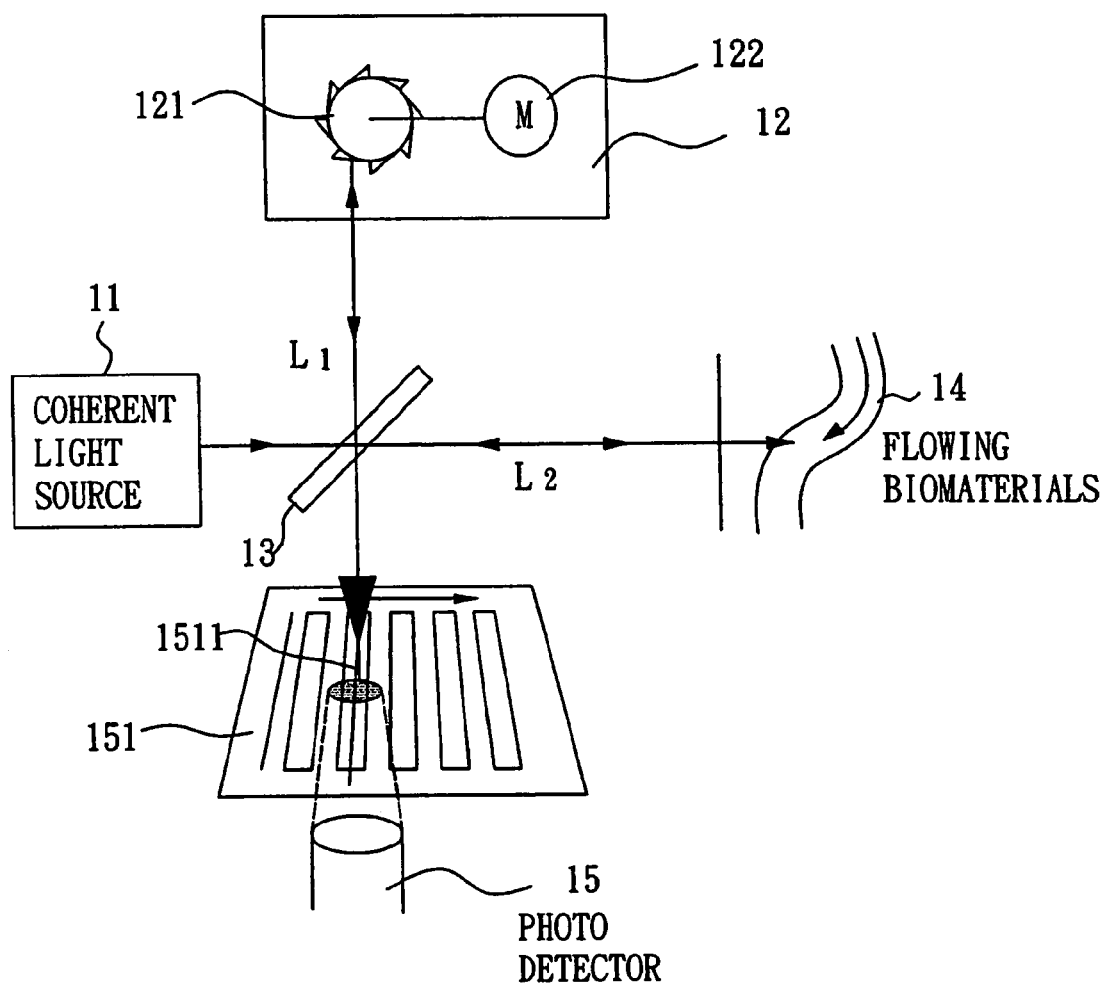
FIG. 1 is a side view of the optical apparatus of the first embodiment of the present invention.

With reference to FIG. 1, there is shown the first embodiment of the optical apparatus of the present invention. The optical apparatus in the first embodiment includes a coherent light source 11, a reference member 12, a splitter 13, flowing biomaterials 14 for measurement, and a photo detector 15. In the present embodiment, the reference member 12 is consisted of a gear 121 and a linear DC motor 122. On part of the surface of the teeth of the gear 121, reflecting layers (or mirrors) are deposited or formed. In the present embodiment, the flowing materials are fluids in subcutaneous tissues or blood capillaries. An auxiliary mask 151 having a slit 1511 is further included in the optical apparatus of the present embodiment for facilitate the formation and detection of patterns and increase the accuracy for measurement. The photo detector is arranged under the bottom of the mask 151 (see FIG. 1).

The coherent light source 11 in the present embodiment is a He—Ne laser with a central wavelength of 632.8 nm. The photo detector of the present embodiment is a CCD-array device. The splitting ratio of light of the splitter of eth present embodiment is 50/50.

As the coherent light source 11 of the present embodiment projects a light beam with an electrical field $E_0$ to the splitter 13, a reference beam and a detecting beam generates. The detecting beam is projected on the flowing biomaterials 14 (i.e. the micro particles or erythrocytes in the subcutaneous tissues or blood capillaries) to be measured and reflected back to the splitter 13. The other beam from the splitter 13, i.e. the reference beam is projected onto the reflecting layers (or the mirrors) on the teeth of the rotating gears 121 and is periodically reflected to the splitter 13.

Figure 3:
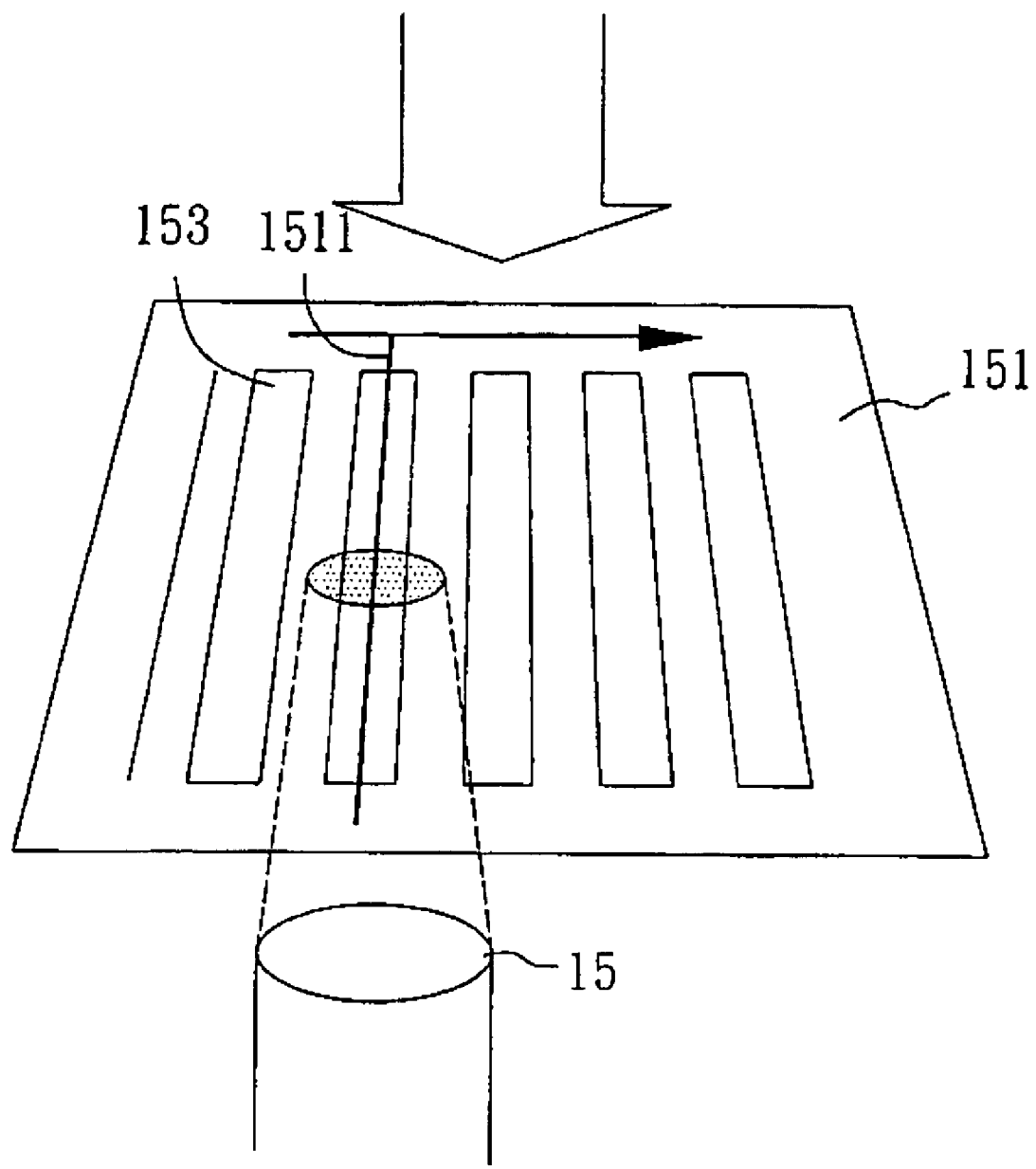
FIG. 3 is an enlarged perspective view of the local portion of the photo detector of the optical apparatus of the first embodiment of the present invention.

The detecting beam and the reference beam is reflected to the photo detector 15 after they go through the splitter 13 and the slit 1511 of the mask 151. A pattern of stripes of interference of the reflected detecting beam and the reflected reference beam forms on the auxiliary mask 151. The interfered light intensity formed by these two beams are detected by the detector after the light go through the slit 1511 on the auxiliary mask 151. In the present embodiment, the width of the slit 1511 is less than that of each stripe 153 (see FIG. 3). After stable pattern of stripes 153 is obtained, the intensity of the stripes can be detected through the photo detector 15.

The frequency of the reference beam reflected from the reflecting layers of the rotating gears 121 is varied according to the rotating speed or velocity of the rotating gears 121 (i.e. Doppler effect). Similarly, the frequency of the detecting beam is also varied according to the flowing velocity of the biomaterials to be measured (i.e. Doppler effect), too.

According to Doppler effect, the difference ($\Delta f$) of the frequency of the original light beam and that of the light beam reflected or scattered by the moving particles can be:

$$\Delta f = \frac{1}{2\pi}(\vec{k}_s - \vec{k}_i) \cdot \vec{V}_s \qquad (1)$$

wherein $\vec{k}_i$ is the wave vector of the incident light beam, $\vec{k}_s$ is the wave vector of reflected light, and is the flowing velocity of moving particles.

As the factors in formula (1) is replaced with the wave vector of the detecting beam for bloods and the wave vector of reference beam for the rotating mirrors of the reference member, the formula (1) will be expressed as formula (2):

$$\Delta f'' = f'_b - f'_s = \frac{1}{2\pi}(\vec{k}'_b - \vec{k}'_s) \cdot \vec{V}'_b \qquad (2)$$

wherein $\vec{k}_b'$ is the wave vector of the detecting beam for bloods, $\vec{k}_s'$ is the wave vector of reference beam for the rotating mirrors of the reference member, and $\vec{V}_b'$ is the relative velocity between the flow velocity of bloods and the velocity of the reference member.

It means that if the distance ($L_1$) between the reference member 12 and the splitter 13, and the distance ($L_2$) between the flowing biomaterials 14 to be measured and the splitter 13 is both within the coherence length, Doppler effect generates in both detecting beam and the reference beam. The difference of frequency can be expressed as formula (2). The stripes pattern 153 caused from the interference by these two beams can be detected through the photo detector 15.

The difference of the frequency $\Delta f'''$ can be obtained by counting the number of the stripes appeared per time unit. In addition, since the wave vector ($\vec{k}_b'$) of the detecting beam for bloods and the wave vector ($\vec{k}_s'$) of reference beam for reference member is known and set before measurement, the relative velocity $\vec{V}_b'$ of blood can be calculated and understood.

Since the motor is controlled by DC input voltage, the relative tangent velocity of the rotating mirrors on the gears can be evaluated through the applied input voltage. Moreover, the tangent velocity of the rotating gears can be obtained if the radius and the rotating speed is known since the tangent velocity is varied by the rotating speed $\omega$ and the radius R according to the formula $V = R \times \omega$.

In addition, the calculation of the stripes can be illustrated in more details. The electrical field of the reference beam and the detecting beam can be expressed as the following formulas, respectively:

$$E_{M1} = E_0 \cos(k_1 x - \omega_1 t)$$

$$E_{M2} = E_0 \cos(k_2 x - \omega_2 t)$$

The synthesized electrical field by these two beams can be:

$$E = E_0[\cos(k_1 x - \omega_1 t) + \cos(k_2 x - \omega_2 t)]$$

After calculation, the synthesized electrical field made by these two beams can be:

$$E(x, t) = E_0(x, t)\cos\frac{1}{2}[(k_1 + k_2)x - (\omega_1 + \omega_2)t]$$

wherein $$E_0(x, t) = 2E_0 \cos\frac{1}{2}[(k_1 - k_2)x - (\omega_1 - \omega_2)t]$$

Since the amplitude of $E_0(x,t)$ in the above formula changes very slowly, the intensity of the light detected by the photo detector 5 can be estimated by following formula:

$$I \propto |E|^2 = E_0(x, t) * E_0(x, t) = 4E_0^2 \cos^2\frac{1}{2}[(k_1 - k_2)x - (\omega_1 - \omega_2)t]$$

or $$I \propto 2E_0^2[1 + \cos[(k_1 - k_2)x - (\omega_1 - \omega_2)t]]$$

wherein $(\omega_1 - \omega_2)$ is the frequency of beats.

Therefore, as the stripes pattern is observed and the stripes stayed on the surface of photo detector without obvious moving through slightly adjusting the input voltage of the DC motor, the velocity of the rotating gears can be very close to the flowing velocity of the biomaterials to be measured. Therefore, the relative flowing velocity can be obtained through calculation. Of course, the accuracy of the measurement can be further improved by unifying the polarity of the detecting beam and the reference beam. In that case, a polarizer is arranged between the coherent light source and the splitter.

Through the illustration above, the relative flowing velocity of the flowing biomaterials can be obtained by adjusting the input voltage of the motor for rotating gears and by counting the frequency of the stripes. Therefore, complicate calculation for the conventional devices for measuring flowing velocity of bloods can be saved.

Figure 2:
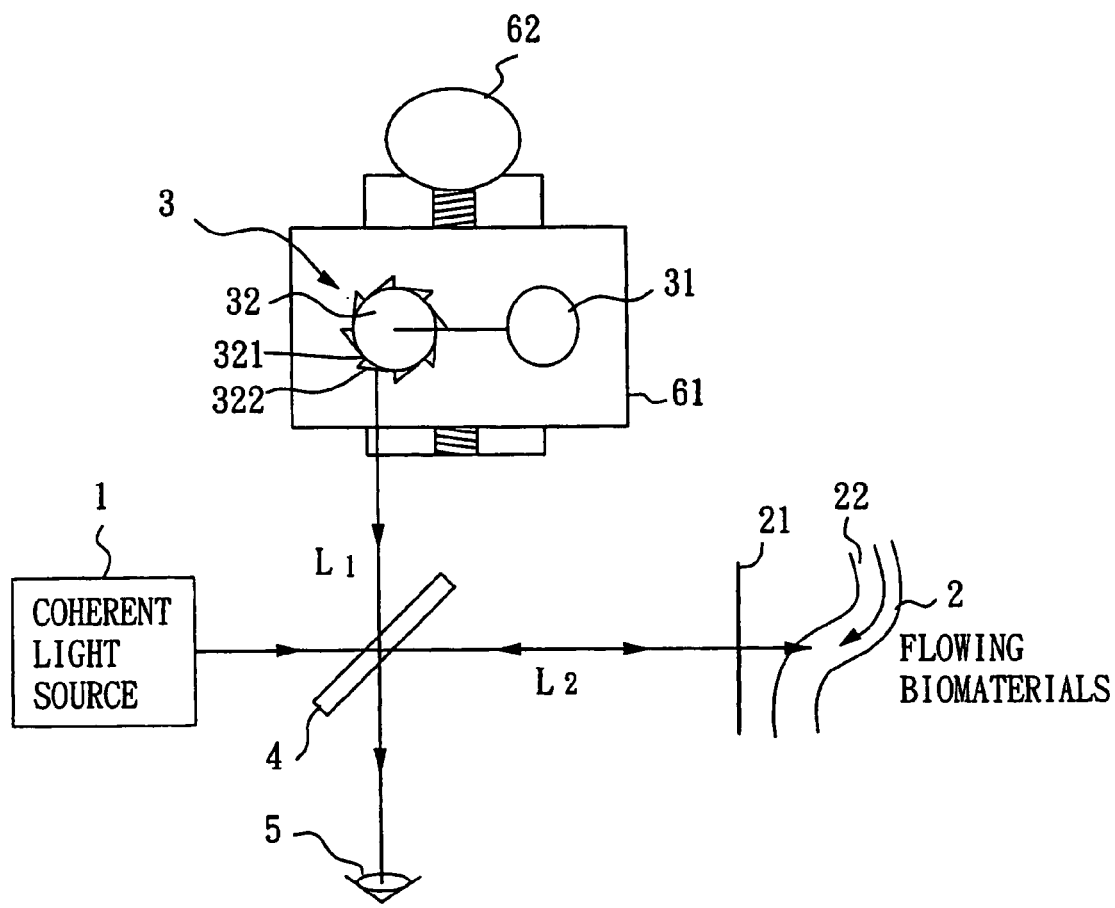
FIG. 2 is a side view of the optical apparatus of the second embodiment of the present invention.

With reference to FIG. 2, there is shown the second embodiment of the optical apparatus of the present invention. The optical apparatus in the second embodiment includes a coherent light source 1, flowing biomaterials 2 for measurement, a reference member 3, a splitter 4, a photo detector 5 and a movable platform 61. The reference member 3 is mounted on the movable platform 61. The reference member 3 can be moved through the assistance of the movable platform 61 according to the line parallel to the light path between the splitter 4 and the reference member 3. In the present embodiment, the reference member 3 is consisted of a gear 32 and a linear DC motor 31. On part of the surface of the teeth 321 of the gear 32, reflecting layers 322 (or mirrors) are deposited or formed. All the elements mentioned above are arranged in a configuration referring to Michelson Interferometer. According to the theorem illustrated in the first embodiment, if the distance ($L_1$) between the reference member 3 and the splitter 4, and the distance ($L_2$) between the flowing biomaterials 2 to be measured and the splitter 4 is both within the coherence length, Doppler effect generates in both detecting beam and the reference beam. In the present embodiment, the flowing materials 2 are fluids 22 in subcutaneous tissues or blood capillaries. An auxiliary mask having a slit is further included in the optical apparatus of the present embodiment for facilitating the formation of patterns and increasing the accuracy for measurement. The photo detector is arranged under the bottom of the mask just as the way described in the first embodiment.

The coherent light source 1 in the present embodiment and the photo detector used in the present embodiment is the same as those in the first embodiment. The stripes patterns generated by the reference beam and a detecting beam is similar to that appeared in the first embodiment. Therefore, the relative velocity or the absolute velocity of the flowing biomaterials can be calculated in a way as described in the first embodiment.

However, since the platform 61 can move the positions or the locations through tiny movement (e.g. 30 µm per movement). More than one position or more than one location can be applied for velocity measurement for flowing biomaterials.

As we know, the intensity of the stripes patterns formed on the photo detector depends on the distance ($L_1$) between the reference member 3 and the splitter 4, and the distance ($L_2$) between the flowing biomaterials 2. The maximum intensity of stripes can be obtained as $L_1 = L_2$. However, if the difference between $L_1$ and $L_2$ is over the coherence length, no stripes patterns will be observed. In other words, if the platform is moved to make the difference between $L_1$ and $L_2$ greater than the coherence length of the coherent light source, no patterns of interference caused by the detecting beam and the reference beam will be observed. It means that the flowing velocity of the biomaterials of old location or old depth before movement cannot be observed. However, only the flowing velocity of the biomaterials of new location or new depth after movement can be observed since only $L_1$ and $L_2$ of the new position after movement can match the equation $L_1 = L_2$. Through this effect for forming stripes pattern on the photo detector, the relative flowing velocity or the absolute flowing velocity of different depth in the subcutaneous tissues or blood capillaries can be measured or calculated easily.

The movement of the platform 61 is driven and controlled by a stepper motor 62 in the second embodiment. The movement of the platform 61 is designed to change the distance ($L_1$) between the reference member 3 and the splitter 4 as the flowing velocity of the biomaterials is measured. Actually, the difference of $L_1$ for each change or each position is around the scale of the coherence length of the coherent light source 1. For example, 30 µm is varied for the movement of platform 61 each time as a light source 1 with a coherence length of 30 µm is applied. As different $L_1$ is scanned, the relative or the absolute flowing velocity of various depths in the subcutaneous tissues or blood capillaries can be measured without complicate computation by using the optical apparatus of the present invention. Moreover, since the absolute flowing velocities can be measured through the optical apparatus of the present invention, the medical information about the flowing velocities of flowing biomaterials can be communicated on the same common base easily. In addition, the optical apparatus of the present invention is a non-intruded device for human body or animals, the observation or the checking for the blood flow can be achieved very easily.

Although the present invention has been explained in relation to its preferred embodiment, it is to be understood that many other possible modifications and variations can be made without departing from the spirit and scope of the invention as hereinafter claimed.

What is claimed is:

1. An optical apparatus for measuring the velocity of flowing biomaterials, comprising:
   a coherent light source for projecting a light beam with low coherent length;
   a reference member having mirrors for periodically reflecting lights thereon;
   a photo detector for receiving photo signals;
   a splitter for splitting said light beam from said coherent light source into a reference beam and a detecting beam;
   wherein said splitter is located between said photo detector and said reference member, said reference beam from said splitter projects on said reference member and reflects back to said photo detector by the refection of said splitter; said detecting beam from said splitter projects on said biomaterials and reflects back to said photo detector by the refection of said splitter; and at least one location of said reference member relative to said splitter is applied as the velocity of said biomaterials flow is measured.

2. The apparatus as claimed in claim 1, wherein said reference member comprises at least a gear for mounting said mirrors; and a motor for driving said gears to rotate for periodically reflecting said reference light to said splitter.

3. The apparatus as claimed in claim 2, wherein said mirrors is mount on the teeth of said gear for reflect said reference light back to said splitter.

4. The apparatus as claimed in claim 3, wherein said mirror are reflecting layers formed on said teeth of said gear through deposition or through coating.

5. The apparatus as claimed in claim 2, wherein said rotation speed of said motor depends on a voltage input to said motor.

6. The apparatus as claimed in claim 1, further comprising a movable platform on which said reference member is mount for changing the positions of said reference members.

7. The apparatus as claimed in claim 1, further comprising a polarizer located between said coherent light source and said splitter.

8. The apparatus as claimed in claim 1, further comprising an auxiliary mask having a slit, wherein said auxiliary mask is located between said splitter and said photo detector.

9. The apparatus as claimed in claim 8, wherein said lights reflected on said photo detector form a pattern of stripes, and the width of said slit is less than a distance between any two adjacent stripes.

10. The apparatus as claimed in claim 1, wherein said photo detector is a charge-coupled-device (CCD).

11. The apparatus as claimed in claim 1, wherein said biomaterials are bloods in vessels.

12. The apparatus as claimed in claim 1, wherein one fixed location of said reference member relative to said splitter is applied as the relative velocity of said biomaterials flow is measured.

13. The apparatus as claimed in claim 1, wherein said low coherent length of said light beam from said coherent light source is less than 100 µm.

14. The apparatus as claimed in claim 1, wherein said coherent light source is an ultrafast laser, a super luminescent diode (SLD), an edge emitting diode laser, an Er-doped super luminescence optical fiber, and a Tm-doped super luminescence optical fiber.

15. The apparatus as claimed in claim 1, wherein the wavelength of said coherent light source is located in the wavelength region of visible light or of near-infrared radiation.

* * * * *